United States Patent
Lin et al.

(10) Patent No.: US 10,421,937 B2
(45) Date of Patent: Sep. 24, 2019

(54) HIGH GAS FLOW RATE BIO-REACTIVE CONTAINER FILTER APPARATUS

(71) Applicant: Saint-Gobain Performance Plastics Corporation, Solon, OH (US)

(72) Inventors: ZhenWu Lin, Pasadena, CA (US); Kenneth James Renfrew, Huntersville, NC (US); Jacob Andrews, Washington, DC (US)

(73) Assignee: Saint-Gobain Performance Plastics Corporation, Solon, OH (US)

( * ) Notice: Subject to any disclaimer, the term of this patent is extended or adjusted under 35 U.S.C. 154(b) by 183 days.

(21) Appl. No.: 15/061,614

(22) Filed: Mar. 4, 2016

(65) Prior Publication Data

US 2016/0257920 A1 Sep. 8, 2016

Related U.S. Application Data

(60) Provisional application No. 62/128,547, filed on Mar. 5, 2015.

(51) Int. Cl.
| | |
|---|---|
| *C12M 3/00* | (2006.01) |
| *C12M 1/00* | (2006.01) |
| *C12M 1/26* | (2006.01) |
| *B01D 63/00* | (2006.01) |

(52) U.S. Cl.
CPC ............. *C12M 33/14* (2013.01); *B01D 63/00* (2013.01); *C12M 23/14* (2013.01)

(58) Field of Classification Search
CPC ...... C12M 29/04; C12M 25/02; C12M 25/16; C12M 41/34; C12M 25/04
See application file for complete search history.

(56) References Cited

U.S. PATENT DOCUMENTS

| | | | | |
|---|---|---|---|---|
| 5,208,161 | A | * | 5/1993 | Saunders ............. B01D 61/142 210/232 |
| 5,882,943 | A | * | 3/1999 | Aldeen .................. B01L 3/502 210/323.2 |
| 6,063,618 | A | | 5/2000 | Weuster-Botz et al. |
| 2005/0282269 | A1 | | 12/2005 | Proulx |

(Continued)

FOREIGN PATENT DOCUMENTS

| | | |
|---|---|---|
| JP | 2012-055226 A | 3/2012 |
| KR | 10-2002-0022286 A | 3/2002 |

*Primary Examiner* — Nathan A Bowers
(74) *Attorney, Agent, or Firm* — Lorusso & Associates

(57) ABSTRACT

A bio-reactive container and filter assembly to improve flow rates and mass transfer without increased pressure. An inlet filter membrane secured to the container defines a container chamber in combination with the container. An inlet filter membrane element may also be secured to the container to provide structural support to the membrane. An outlet membrane secured to the container defines a container chamber in combination with the container. An outlet filter membrane element may also be secured to the container to provide structural support to the outlet membrane. Inlet and/or outlet filters and/or filter elements are constructed to significantly increase surface area available for fluid and/or gas ingress and/or egress. Single and double layer membranes with mixtures of hydrophobic and hydrophilic characteristics are used to maximize perfusion and gasification/degasification of bio-reactive containers.

20 Claims, 9 Drawing Sheets

(56) References Cited

U.S. PATENT DOCUMENTS

| | | | |
|---|---|---|---|
| 2008/0227176 A1* | 9/2008 | Wilson | C12M 23/08 |
| | | | 435/243 |
| 2009/0181450 A1* | 7/2009 | Ribault | C12Q 1/24 |
| | | | 435/287.1 |
| 2010/0323435 A1* | 12/2010 | Boateng | C10B 49/10 |
| | | | 435/289.1 |
| 2011/0287404 A1* | 11/2011 | Niazi | B65B 63/08 |
| | | | 435/1.1 |
| 2012/0129252 A1 | 5/2012 | Seubert | |
| 2014/0273063 A1* | 9/2014 | Baust | G01N 33/5008 |
| | | | 435/29 |
| 2016/0075981 A1* | 3/2016 | Lee | C12M 29/04 |
| | | | 435/257.1 |

* cited by examiner

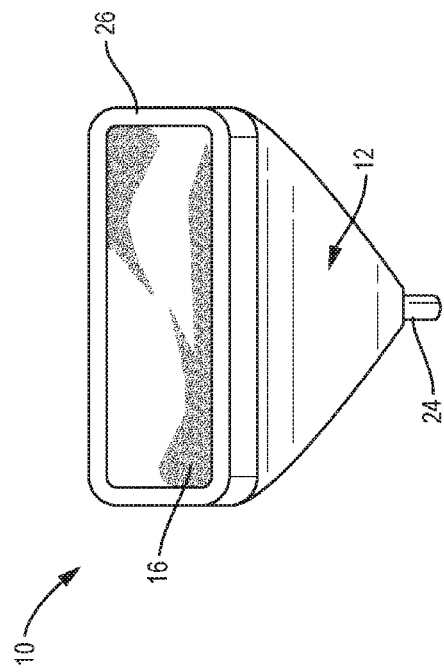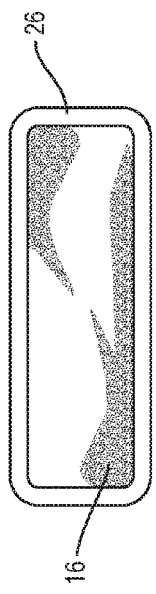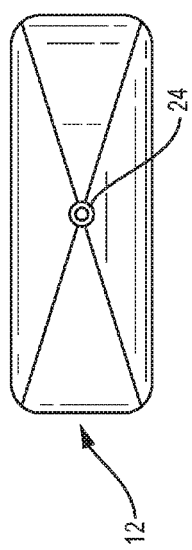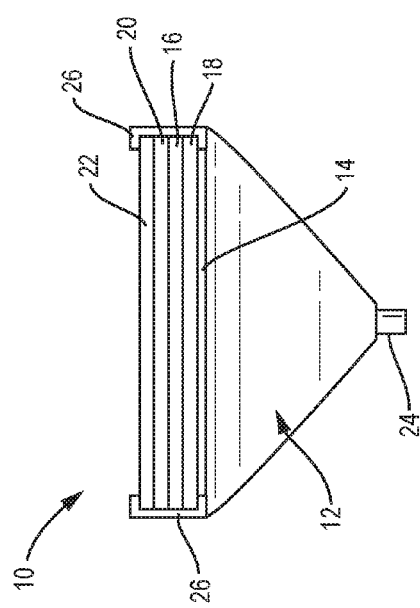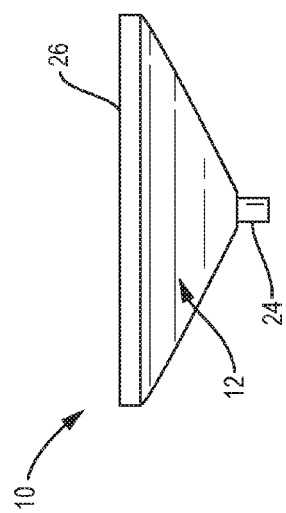

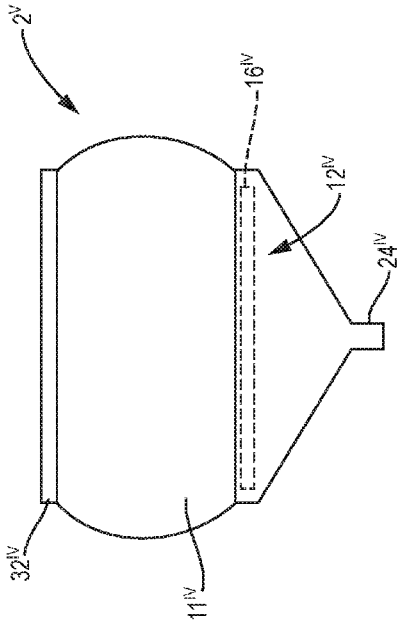
FIG. 9
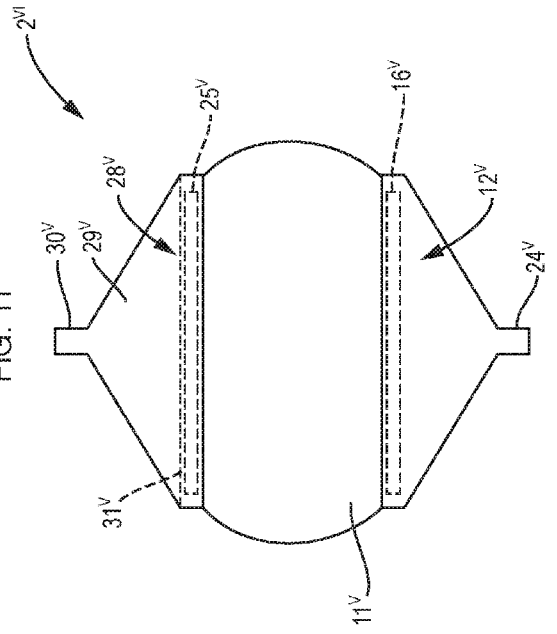
FIG. 10
FIG. 11
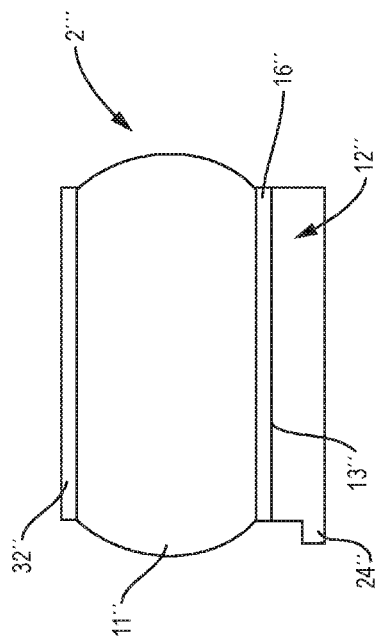
FIG. 12

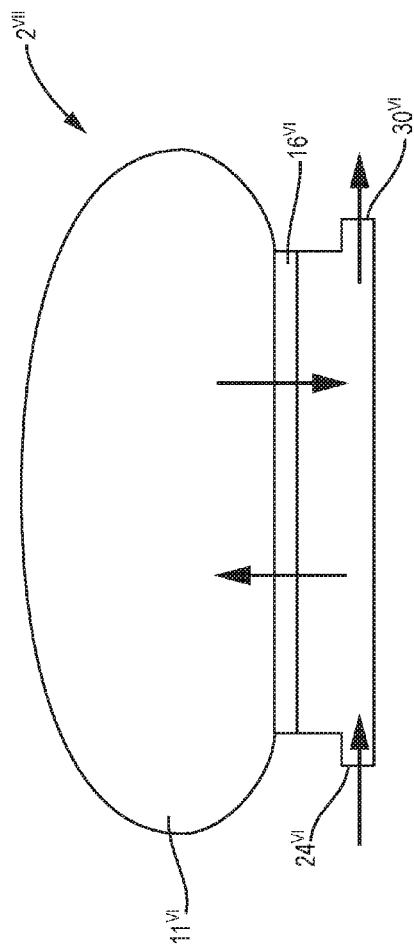
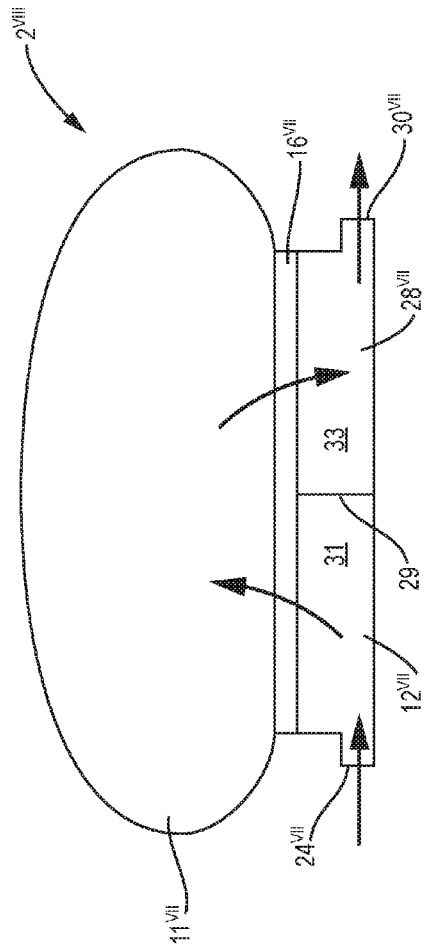

HIGH GAS FLOW RATE BIO-REACTIVE CONTAINER FILTER APPARATUS

CROSS REFERENCE TO RELATED APPLICATIONS

A claim of benefit is made to U.S. Provisional Patent Application Ser. No. 62/128,547, filed Mar. 5, 2015, the contents of which are incorporated in their entirety herein by reference.

FIELD OF THE DISCLOSURE

The disclosure relates to filters suitable for use with cell culture bags or bio-reactive containers as well as other vented bags used for mixing, storing, transporting and cell culturing, among other uses in a variety of industries. The filters are structured to improve gas and/or other fluid flow and mass transfer into and out of the containers. More particularly, the disclosure concerns barrier filters secured directly to bio-reactive containers to improve efficiency, control, adaptability to lower pressure limits, and to simplify container design.

BACKGROUND OF THE DISCLOSURE

Biobags, also known as cell culture bags or bio-reactive containers, are used, among other purposes, to culture cellular material in a sterile environment. To accomplish this intended purpose, gases or other fluids necessary to promote cell growth and division must be introduced into, and removed from, the biobag containers. A common bio-reactive container configuration, such as that shown designated generally as 7 in FIG. 15, includes a bag-like structure 1 made from pliable, flexible synthetic materials such as polyethylene or polypropylene to provide a substantially air-tight fluid-impermeable environment in which to grow and expand cell cultures in a sterile manner.

Access to the container inner chamber is provided commonly by at least one inlet port 2 and one outlet port 3. Containers may also have multiple inlet and outlet ports-some dedicated to liquids and others dedicated to gases. The ports are often formed as cylindrical appendages extending from the containers. Each port may be structured with connectors for connecting to fluid and/or gas sources and may be formed as integral or modular components of the containers. Means to block fluid and/or gas flow into and/or out of the container, e.g., check valves and the like, may be provided at each port. Liquids, e.g., sterilized water, nutrient fortified solutions and the like may be transferred into the container from the inlet side. Gases, e.g., oxygen for aeration, filtered air and nitrogenous-bearing gases and the like may also be transferred into the container to promote cell culture development.

Excess liquids and/or gasses introduced into the containers may require removal from the containers to further promote desired cell culture development. Gaseous and fluid-based byproducts and wastes derived from cellular respiration and the like may also require removal from the containers. Product(s) derived from the cellular activity within the containers and desired for harvesting will also need to be removed from the containers. One or more outlet ports may be provided to permit the removal of such substances.

One significant problem with bio-reactive containers is their sensitivity to fluid and/or gas pressure. Bio-reactive containers often have low burst pressure ratings on the order of about 1-5 psi and often have recommended operational pressures on the order of about 0.2-0.5 psi. Any significant fluid or gas pressure introduced into the containers, above the burst pressure limit, will likely lead to rupture or failure of the containers. To address this issue, one or more vent filters 5 may be secured to the containers with the appropriate flow rate versus pressure-drop performance to allow exhaust gas to escape without over-pressurizing the containers. The vent filter serves as a sterile barrier between the internal container chamber and the environment outside of the container so as to prevent microbial contamination from transferring from the internal chamber to the outside environment and vice versa. The filter also functions to prevent the egress of non-sterile liquids and/or gases depending upon the application.

It is similarly necessary to place a sterilizing device in the fluid and/or gas inlet lines. To accomplish the desired sterilizing effect, a filtering device 4 is often placed in the fluid and/or gas infusion lines downstream of a pump or regulator used to drive and control fluid flow upstream of the container. The inlet filter also serves as a sterile barrier between the internal container chamber and the environment outside of the container so as to prevent microbial contamination from transferring from the internal chamber to the outside environment and vice versa.

Due to the common tubular inlet and/or outlet configurations that can range from about 0.25 inches to about 1 inch in diameter, the filters used for this application are contained in filter capsules, e.g., filter capsule 6 for outlet filter 5, that include inlet and outlet ports dimensionally complimentary to the tube/piping and/or inlet systems of the bio-reactive containers and with appropriate connection fittings, such as barbed fittings, where necessary. The relatively small cross-sectional area of the inlet tubing systems creates a further limitation on fluid and/or gas flow rate and bulk mass transfer into the containers.

A similar flow-rate restriction is experienced on the outlet side of the bio-reactive container. Outlet ports, structured and dimensioned similar to the inlet ports, create a flow restriction with respect to liquids and/or gases removed from the containers. Filters incorporated into the outlet tube system also contribute to the flow restriction of liquids and/or gases. This may result in the development of unwanted backpressure that further impedes inlet flow and may compromise the speed and efficiency of cell culture formation as well as the production of desirable products derived from cell cultures.

Smaller capsules may incorporate flat-sheet filter membranes that are relatively low in cost, but limit the potential fluid-receiving surface area to less than 100 cm$^2$. Applications requiring larger filter surface areas often incorporate pleated filter designs to increase surface area within a similar cross-sectional area. Pleated filters, however, increase cost and add undesirable weight to the bio-container. Further, in the case of exhaust gas exiting from the bio-container, the tubing commonly used to connect filters to the bio-container can present a problem when moisture contained in the humid gas condenses in the tubing. The formed liquid can make its way into the filter assembly and block the flow of air through the hydrophobic vent filter membrane.

What is needed is a bio-reactive container filter configuration that maintains low cost and significantly increases available filter surface area to maximize fluid flow rates. What is also needed is a filter configuration that permits the use of low fluid and/or gas pressures to protect container integrity without compromising fluid flow rates and/or mass transfer rates. What is further needed is a filter configuration that prevents the trapping of liquid within connective tubing and within the filter assembly itself. These and other objects of the disclosure will become apparent from a reading of the following summary and detailed description of the disclosure.

SUMMARY OF THE DISCLOSURE

In one aspect of the disclosure, a flexible walled bio-container or cell culture bag is provided with an inlet filter element secured directly to the container, the combination of which defines a cell culture chamber so as to function as a filtration barrier to separate internal and external environments defined by the container and the inlet member. The inlet barrier member includes a filter structured to sterilize gases and/or liquids transferred into the container to support and promote cell culture propagation in an otherwise sterile environment without any significant compromise to fluid and/or gas flow rates.

In another aspect of the disclosure, a flexible walled bio-container is provided with an outlet filter element secured directly to the container, the combination of which defines a cell culture chamber. The outlet filter element functions as a filtration barrier that separates internal and external environments, but permits liquids and/or gasses to exit the container without any appreciable development of back pressure. The outlet filter element may be structured to vent to the atmosphere, or may be controlled and contained with the use of an outlet port.

In a yet further aspect of the disclosure, a bio-container is structured with an inlet filter element that functions as a filtration barrier and an outlet filter element that functions as a filtration barrier to control and sterilize liquids and/or gasses introduced into, and/or exiting out of, the container. The inlet and outlet filters may be formed both on a top end of the container, both on a side or sides of the container, both on a bottom end of the container, or structured in multiple orientation combinations relative to top and bottom ends and sides of the container. Any of the described aspects of the disclosure will reduce pressure values needed to prevent pressure buildup beyond the container burst pressure limit without significant compromise of the desired fluid and/or gas flow rates and mass transfer rates.

In a still further aspect of the disclosure, a bio-container is structured with an inlet and/or an outlet filter element with a dual layer hydrophilic/hydrophobic membrane secured in the inlet and/or outlet, or between the inlet and/or outlet and the bio-container. The configuration prevents the bulk flow of liquid and gas across the membrane while permitting the diffusive transfer of gas into, or out of, the liquid phase inside the bio-container. In yet a further embodiment of the disclosure, a single hydrophobic membrane may be used at the outlet side to improve the efficiency of degasification.

These and other aspects of the disclosure will become apparent from a review of the appended drawings and a reading of the following detailed description of the disclosure. It should be understood that any drawings described herein are included for illustrative purposes and should not be considered as limiting the overall scope of the disclosure.

BRIEF DESCRIPTION OF THE DRAWINGS

FIG. 1 is a side elevational view of a bio-reactive container inlet member with filter according to one embodiment of the disclosure.

FIG. 2 is a top perspective view of the container inlet member shown in FIG. 1.

FIG. 3 is a side elevational view of the inlet member shown in FIG. 1.

FIG. 4 is a top plan view of the inlet member shown in FIG. 1.

FIG. 5 is a bottom plan view of the inlet member shown in FIG. 1.

FIG. 9 is a side elevational view of a bio-reactive container with a filter inlet and a filter outlet according to a still further embodiment of the disclosure.

FIG. 10 is a side elevational view in partial phantom of a bio-reactive container with a filter inlet and a filter outlet member according to yet another embodiment of the disclosure.

FIG. 11 is a side elevational view in partial phantom of a bio-reactive container with a filter member inlet and a filter outlet according to another embodiment of the disclosure.

FIG. 12 is a side elevational view in partial phantom of a bio-reactive container with an inlet member and an outlet member according to still another embodiment of the disclosure.

FIG. 13 is a side elevational view of a bio-reactive container with a combined filter member inlet and outlet according to further embodiment of the disclosure.

FIG. 14 is a side elevational view of a bio-reactive container with a segmented combined filter member inlet and outlet according to a yet further embodiment of the disclosure.

DETAILED DESCRIPTION OF THE DISCLOSURE

Figure 6:
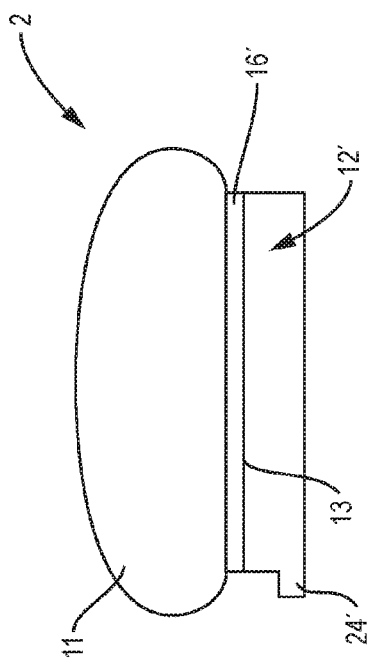
FIG. 6 is a side elevational view of a bio-reactive container with filter inlet according to another embodiment of the disclosure.

Referring to FIGS. 1-5, in one aspect of the disclosure, a bio-reactive container inlet element structured for adaptation to a bio-reactive container is shown designated generally as 10. As used herein, bio-reactive container shall mean any enclosed container having pliable and/or rigid walls and at least one port whereby the container is structured and adapted for use to culture, store, process, contain, transport, and/or for other purposes, cells and/or similar biological materials, water, buffers, nutrients, culture media, serum, API's, therapeutic products and the like. As used herein, a bio-reactive container inlet element or filter support assembly shall mean an element or assembly constructed to support and/or contain a filter wherein the element is secured to a bio-reactive container in place of, or as an adjunct to, a bio-reactive container inlet. Inlet element 10 is shown as having a general rectangular shape at the inlet element/container junction, but may be formed to conform to any regular or irregular geometric shape to accommodate any bio-reactive container configurations and/or any configurations of larger assemblies to which the bio-reactive container may be affixed.

Inlet element 10 (and/or any outlet element disclosed herein), may be secured to a bio-reactive container at any position of the container, e.g., top, bottom, sides and any combination or intersection of these container portions. It should be understood that placement of inlets/outlets at certain selected positions may be more advantageous than others depending upon factors such as the application made of the bio-reactive container and its spatial orientation, particularly with respect to gravity. For example, an inlet element placed on the top of a bio-reactive container may be advantageous when liquids and/or gases introduced into the container are intended to flow downwardly into the container via gravity without pressure assistance.

In the embodiment shown in FIGS. 1-5, a rigid filter support/inlet funnel structure shown designated generally as 12 provides the main support structure for the element. Support structure 12 has portions that define an inlet 24 that may be cylindrical in cross-section, or may be structured with different cross-sectional shapes and features including barbs, threading, locking features and the like. Inlet 24 may also be shaped and structured for adaptation to receive conventional quick connects (not shown), tri-clamps (not shown) or like connection devices to secure inlet 24 to fluid and/or gas supply sources. A frustoconical section of support structure 12 expands from a relatively narrow end proximate, and in fluid communication with, inlet 24 to a relatively broad distal end structured to accommodate and ultimately support a filter membrane 16. The distal end of support structure 12 forms a filter membrane support surface or filter seat 14.

Seat 14 may be formed integrally with support structure 12, or may be modular in construction to be secured to structure 12 via thermal bonding, solvent bonding, adhesive bonding, mechanical fasteners and like bonding methods. Seat 14 may be formed to be substantially planar to permit a substantially flat filter membrane to be seated against and/or secured to the filter receiving surface. An internally recessed shoulder may also be formed around the perimeter of seat 14 to receive filter membrane 16 and any additional support structures. In this configuration, an outer edge of seat 14 may define a perimeter wall that prevents lateral or radial displacement of membrane 16 and any additional support structures secured to structure 12.

As the total surface area of filter membrane 16 is significantly greater than the relatively small peripheral segment of the membrane that registers against filter seat 14, a substantial portion of membrane 16 is left without structural/mechanical support. Although a rigid filter may not require supplemental support, an optional lower membrane support 18 may be used to provide additional support and add structural integrity to the membrane regions other than the membrane peripheral binding/attachment region. Supportive structures, particularly those positioned on the downstream side of a filter element (disclosed in detail below), are advantageous when relatively high fluid and/or gas pressures are expected to be implemented, or the material being introduced into a bio-reactive container is a liquid having a much higher viscosity than a gas.

The material used to fabricate support 18 may be the same as the material used for the filter, or from different materials as disclosed herein. For embodiments that employ a membrane support structure, support 18 will define dimensionally at a minimum, at least a perimeter "band" that underlies the perimeter portion of membrane 16 that functions as at least part of the membrane's binding/attachment region. This explanation of supportive structures is generally applicable to any port, whatever its designated function. Supportive structures, such as those disclosed herein as being downstream of the membrane relative to the direction of flow, will provide the kind of support that may be necessary unless reverse pressurized for any reason. It then becomes more advantageous, and even possibly necessary, to provide supportive structures on an upstream side.

The support "band" may extend laterally (as a flange to facilitate attachment to the bio-reactive container) and/or radially inwardly from the perimeter and/or shoulder of seat 14 to provide any desired filter membrane structural support. The "band" may be an integral part of the overall support constructed to support some or all regions of membrane 16. Support 18 must be structured to permit the free passage of liquids and/or gases introduced into the bio-reactive container. In one embodiment, support 18 may cover the entire area of membrane 16 to provide maximum support. With this embodiment, support 18 should be constructed from a porous material having a pore size greater than or equal to the pore size of membrane 16. Supports fabricated with porosities greater than the porosity of membrane 16 and with pore sizes greater than the pore size(s) of membrane 16 (often 0.2 μm but can be from about 0.05 micrometers to about 1.0 micrometers based on liquid ratings or could be HEPA- or ULPA-rated) should reduce any negative impact on flow. To maximize the support to membrane 16, the pore size of support 18 must be kept small enough (however, at least as large as the pore size of membrane 16), and the porosity kept low enough, to provide the desired support to the membrane.

In a further embodiment, support 18 may be formed with defined solid regions (having regularly or irregularly shaped geometric boundaries) to supply site specific support, particularly when the surface area involved is relatively large compared to the thickness of the membrane and the support. Solid sections may be formed, in some embodiments, on the periphery of the support where additional thermal bonding, or other forms of bonding to the membrane, and/or the structural components of container 2, inlet element 10 and/or structure 12 may be implemented. Solid regions may also be formed in non-peripheral segments of the support to coincide with specific regions of a supported membrane, particularly one comprised of different hydrophilic and hydrophobic regions. The solid regions are strategically placed or formed in support 18 to provide direct support to a particular region(s) of membrane 16. Such modifications with uniform/regular or random patterns of solid regions and porous regions can resemble patterns such as a checkerboard pattern to impart the desired support and porosity features.

Support 18 may also be structured from membrane material with hydrophilic, hydrophobic, or combined hydrophilic/hydrophobic characteristics. The hydrophilic, hydrophobic or combined characteristics may be structured to match the characteristics of membrane 16, area for area, or may be structured to differ from the characteristics of the membrane in some or all areas to impart specific control over the flow of fluids and/or gases traversing the membrane and support. It should be noted and understood by those of skill in the art that matching of hydrophobic characteristics may be more important when dealing with the control of gas flow as opposed to fluid flow.

To provide even further structural integrity, particularly in reverse-flow situations, an upper membrane support 20 may be applied above membrane 16 in similar fashion to lower support membrane 18. Upper membrane support 20 may be constructed from the same material as membrane 16 and lower membrane support 18, or may be constructed from different materials depending upon the intended function. Materials including Polyethylene (HDPE/LDPE), Polyester (such as Polyethylene terephthalate (PET)), Polypropylene, Ethylene vinyl acetate (EVA), Nylon, Fluorinated ethylene propylene (FEP), Polyvinylidene fluoride (PVDF), Polytetrafluoroethylene (PTFE), as well as other materials disclosed herein and/or known in the art may be used to construct the various components of inlet element 10. Upper support 20 may be structured as a perimeter band to further secure the edges of filter membrane 16, and may include additional structural features such as modular or integral bars or rods extending across the opening defined by the band to increase rigidity and membrane support. The pattern of bars and/or rods for the various supportive structures disclosed herein may include illustratively, all the embodiments disclosed herein including those shown illustratively in FIGS. 17 through 22 (disclosed in detail below).

To further support and protect membrane 16, an optional upper rigid or non-porous support 22 may be secured to a top surface of membrane 16, or to a top surface of upper membrane support 20, if used, or to another component of inlet element 10. Support 22 may be constructed from materials similar to those used for support structure 12, or may be constructed from different materials such as rigid plastics and non-porous films that impart the desired rigidity or flexibility to accommodate the rigidity or flexibility characteristics of the bio-reactive container material, or as dependent upon the specific application and conditions of use. Suitable materials include Polyethylene (HDPE/LDPE), Polyester (such as PET), Polypropylene, Ethylene vinyl acetate (EVA), Nylon, FEP, PVDF, PTFE, as well as other materials disclosed herein and/or known in the art may be used to construct the various components of inlet element 10.

When selecting a material, it is important to take into consideration whether or not any reaction may take place between the rigid support material and the bio-reactive container material, with particular consideration about the liquids and/or gases that may be introduced into the container. The selected material should not react with, or be degradable by, any introduced liquids and/or gases. As previously noted, it is also important to take into account the method used to bind the various layers together. If thermal bonding is to be used, as is well known in the art, the materials selected for rigid support 22 should be compatible to the materials used for other layers so as to permit the use of thermal bonding.

Figure 16:
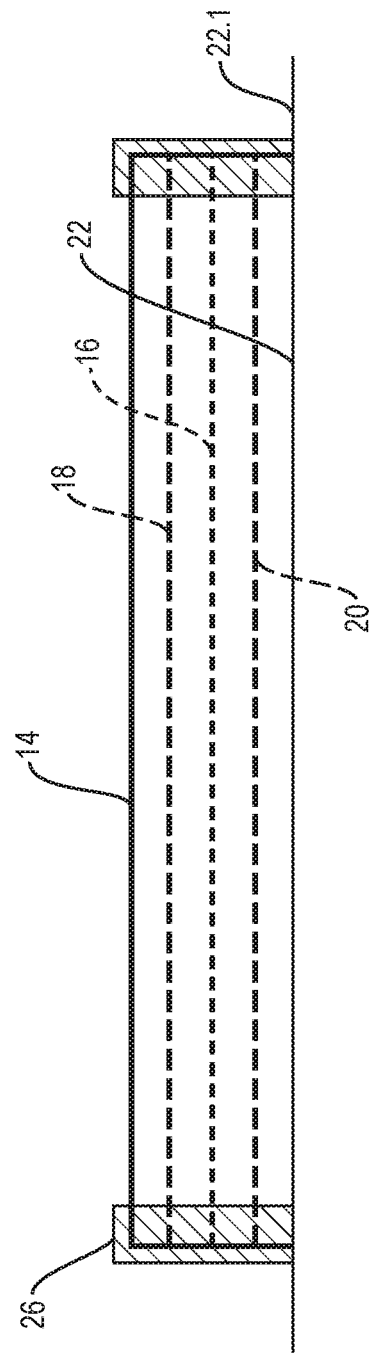
FIG. 16 is a side sectional view in partial phantom of a filter support assembly according to one embodiment of the disclosure.

As shown in FIG. 16, rigid support 22 may include a flange 22.1 extending laterally from the support to provide a broader surface for connection to a bio-reactive container. The flange should be made from a material suitable for attachment to the container, or at least one layer of the container. As is well known in the art, some bio-reactive containers are constructed from multiple layers in which different materials may be used for the different layers. The material selected for rigid support 22 should be compatible with the container layer to which it will be secured. This is particularly important when the method used to secure the assembly to the container is thermal bonding. As such, flange 22.1 may be secured to an outer layer, inner layer, and/or an intermediary layer, whichever is made from a compatible material. The orientation of the assembly shown in FIG. 16 may also be subject to multiple orientations relative to the bio-reactive container in which the membrane and supporting layers are positioned inside the bio-reactive container when secured to the container, positioned outside the container, or positioned partially inside and partially outside the container's inner chamber.

At a minimum, rigid support 22 is structured as a perimeter "band" with, or without one or a plurality of rods, slats or perforations. The use of rods, slats and/or perforations/bores enables the construction of support structures that balance the need for structural support of the center portion of membrane 16 without creating any appreciable impediment to gas and/or fluid flow into the bio-reactive container. When a plurality of rods or slats are used, the rods or slats may be oriented to form a grid (e.g., FIG. 19), with each rod or slat extending substantially orthogonally or angularly from a side or end of the support. The rods and/or slats may be integral or modular relative to the perimeter "band." Such configurations permit the application of structural support to the center portion of membrane 16 without creating any appreciable impediment to gas and/or fluid flow into the bio-reactive container.

Figure 17:
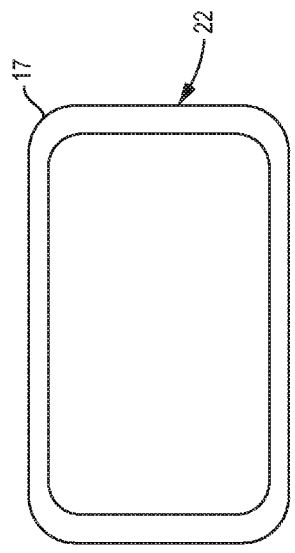
FIG. 17 is a top view of a filter support structure according to one embodiment of the disclosure.

Referring now to FIG. 17, in one embodiment of the disclosure, rigid support 22 forms a ring or band 17 to provide structural support to the membrane 16 peripheral binding region. As with other components of the disclosure, rigid support 22 is secured to membrane 16, or upper support 20, if used, or to another component of inlet element 10 via thermal bonding, sonic bonding, adhesive, mechanical fasteners and the like. This embodiment is particularly useful when additional support of the central areas of membrane 16 is not needed so as to permit maximum unimpeded flow past rigid support 22.

Figure 18:
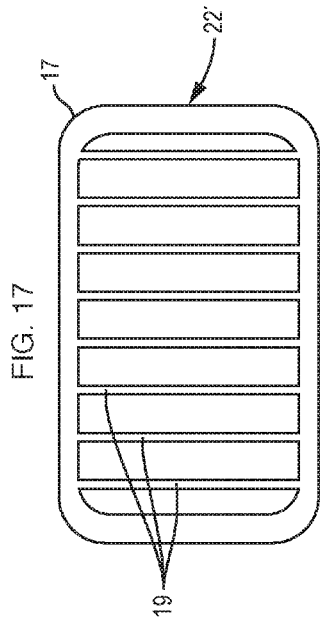
FIG. 18 is a top view of a filter support structure according to another embodiment of the disclosure.

Referring now to FIG. 18, in another embodiment of the disclosure, a rigid support 22' includes band 17 to provide support to the membrane 16 peripheral binding region as well as additional membrane support in the form of substantially parallel struts 19 formed integral with, or secured to, perimeter band 17. As used herein, features assigned the same reference character number with differently primed or unprimed designations are similar features in different aspects or embodiments of the disclosure. This configuration provides uniform support along the length of membrane 16 that extends over and across struts 19. The spacing of struts 19 can be uniform, or may be altered to be non-uniform or irregular so as to provide specific support to specific regions of membrane 16.

Figure 19:
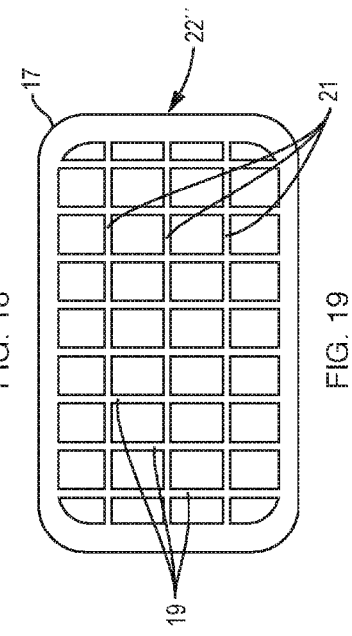
FIG. 19 is a top view of a filter support structure according to yet another embodiment of the disclosure.
Figure 23:
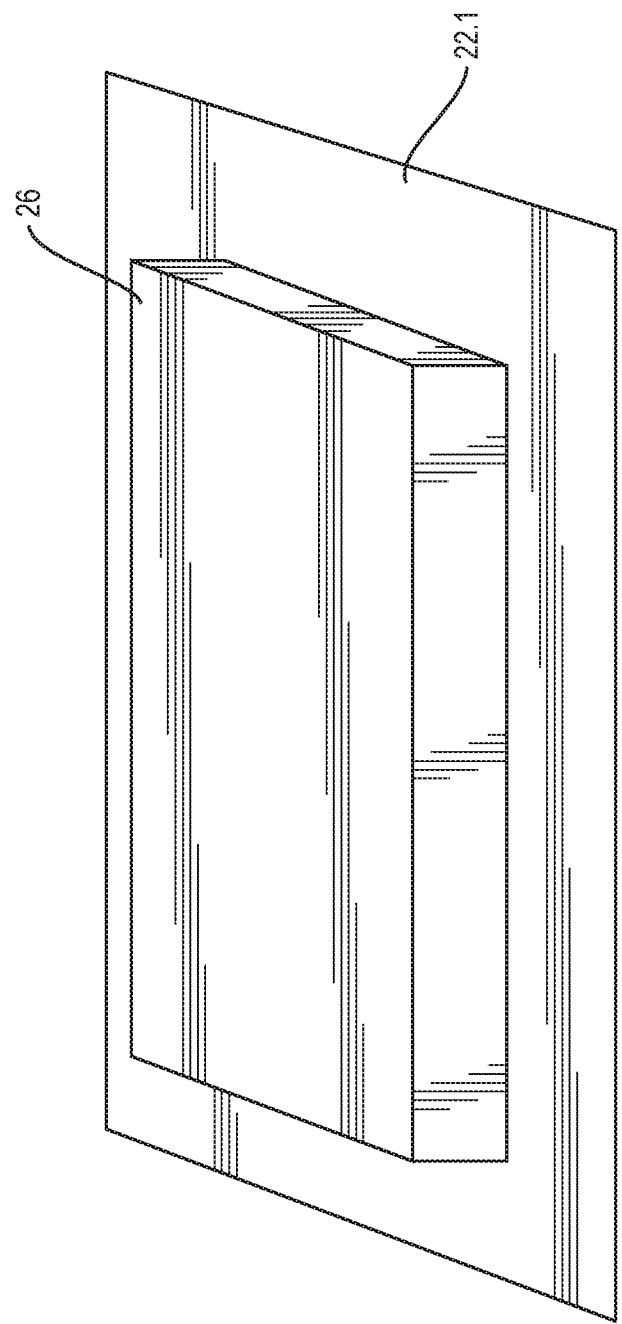
FIG. 23 is a top perspective view of the filter support assembly shown in FIG. 16.
Figure 24:
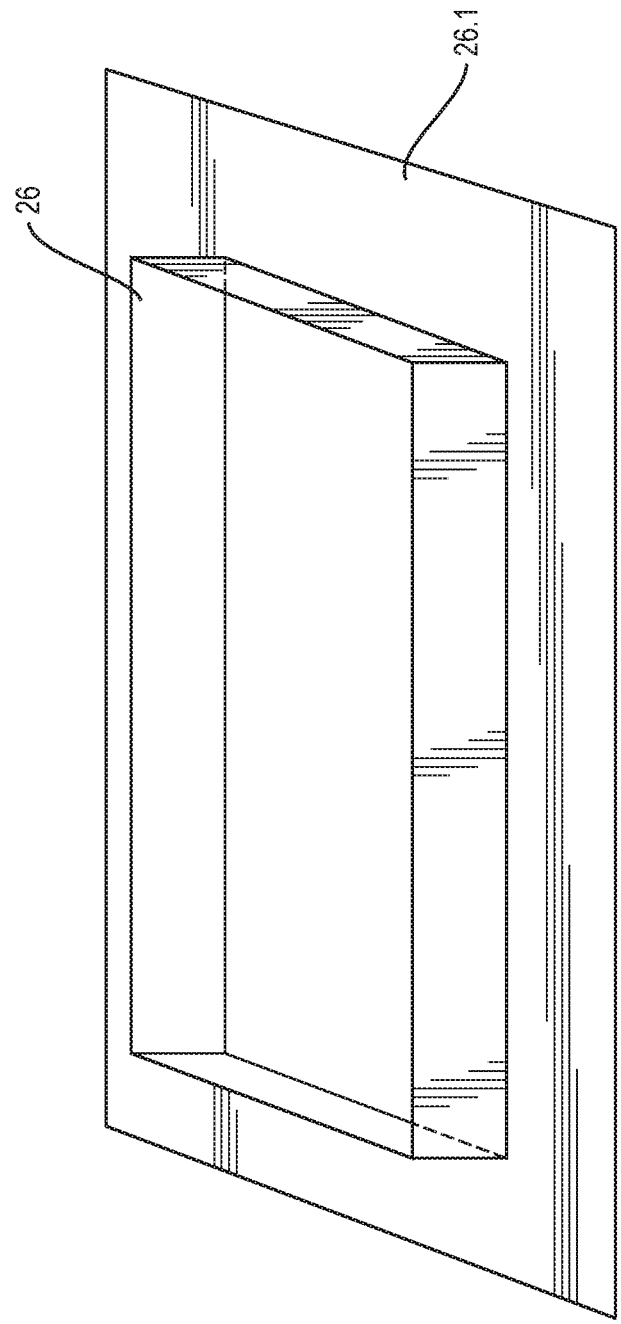
FIG. 24 is a top perspective view of a flange and a sealing band of the filter support assembly shown in FIG. 16.

Referring now to FIG. 19, in a further embodiment of the disclosure, a rigid support 22" is constructed similarly to support 22' with the addition of a plurality of cross struts 21 arranged in a substantially parallel orientation with each cross strut oriented substantially orthogonal to struts 19 to form a grid pattern. This configuration provides additional support over that provided by support 22' when more support is needed. It should be understood that the orientation of struts 19 and cross struts 21 relative to the sides or ends of support 22' and as to each other may be angular rather than orthogonal as shown. It should also be understood that the spacing of struts 19 and cross struts 21 may be uniform, or non-uniform/irregular so as to bias support to specific regions of membrane 16.

Figure 20:
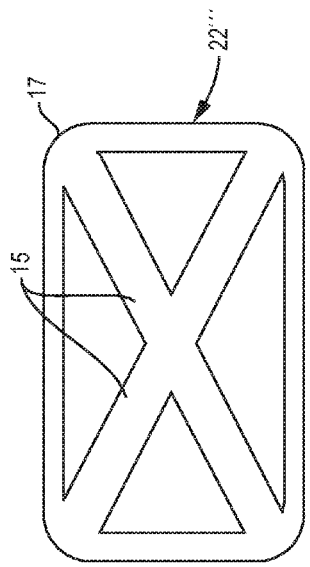
FIG. 20 is a top view of a filter support structure according to still another embodiment of the disclosure.

Referring now to FIG. 20, in a yet further embodiment of the disclosure, a rigid support 22''' is shown having a perimeter band 17 to which two diagonal struts 15 are positioned to intersect the corners of band 17 and cross at a substantial center point of support 22'''. This configuration provides additional support focused on the center of the adjacent membrane 16. The diagonal struts may be integral or modular relative to band 17. It should be understood that the endpoints of diagonal struts do not have to intersect the band corners, but may intersect the sides or ends of band 17. It should also be understood that the diagonal struts do not have to intersect each other at the substantial center of adjacent membrane 16, but may be offset from the center, if needed for a particular application.

Figure 21:
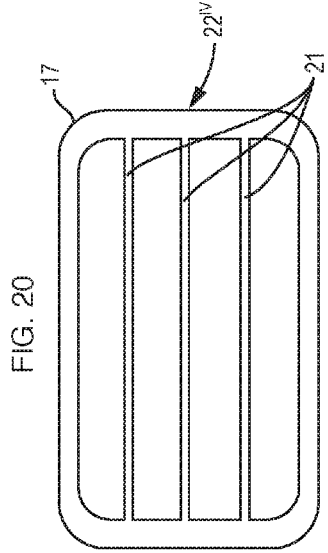
FIG. 21 is a top view of a filter support structure according to a further embodiment of the disclosure.

Referring now to FIG. 21, a support $22^{iv}$ having a perimeter band 17 with a plurality of cross struts 21 arranged in a substantially parallel orientation is shown. This provides support similar to that provided by support 22' except the structural support is directed along the longer dimension (length) rather than the shorter dimension (width) of the support. The struts may be spaced uniformly or irregularly as required by any particular application.

Figure 22:
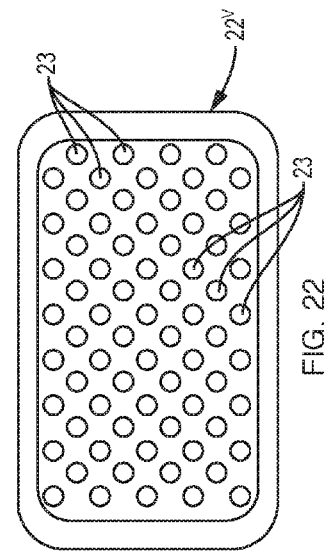
FIG. 22 is a top view of a filter support structure according to a yet further embodiment of the disclosure.

Referring now to FIG. 22, a rigid support $22^v$ having a substantially solid structure with a series of bores 23 formed in the support is shown. The orientation of the bores is shown with a uniform pattern of rows of bores with adjacent rows being offset from the rows before and/or after. This provides maximum support except for those embodiments that include a solid film support. It should be understood that the pattern of bores may by uniform or irregular, e.g., concentrated in different portions of the support to facilitate fluid/gas flow as required by a particular application.

The layers or materials (filter membrane, support membranes, rigid support) form a membrane assembly, inlet element 10, which may be secured via thermal or sonic bonding. Adhesives and the like may also be used. To provide added structural integrity to the layers, a sealing band 26 shown in FIGS. 1, 16, 22 and 23 may be superposed about the layers and heat shrunk, thermally or sonically welded and/or adhered to the various layers. Suitable materials for sealing band 26 include Polyethylene (HDPE/LDPE), Polyester (such as PET), Polypropylene, ethylene vinyl acetate (EVA), Nylon, FEP, PVDF, PTFE, adhesive/potting materials such as urethanes, other materials disclosed herein as well as other materials known in the art may be used to construct the various components of inlet element 10.

In another aspect of the disclosure, a bio-reactive container assembly shown designated generally as 2 in FIG. 6 includes a filter support member 12' with a laterally extended inlet port 24'. Support member 12' is structured to be rigid with a substantially planar surface 13 dimensioned to receive a filter membrane 16'. Membrane 16' is secured between member 12' and bio-reactive container 11. With this configuration, the combination of support member 12' and filter 16' define a substantial portion of the bottom of container 11 so as to improve and maximize bulk mass transfer into container 11. The combination may form and define from about 5% to 100% of the bottom surface of bio-reactive container assembly 2.

Support member 12' may further define a perimeter shoulder dimensioned to further receive and secure membrane 16'. Support member 12' may also have portions defining rods or slats that extend between points on the perimeter shoulder to provide added structural support for membrane 16'. The rods or slats may be integral to, or modular relative to, the perimeter shoulder. The pattern of features may mimic those of rigid support 22 and the various different embodiments shown in FIGS. 17-22, the descriptions of which are incorporated here.

If rods or slats are not incorporated into support member 12', or if rods or slats are provided and additional membrane support is required, similar to the embodiment shown in FIGS. 1-5, additional filter membrane support structures may be incorporated into the assembly to provide added structural support to membrane 16'. More particularly, a bottom filter support 18' similar in construction to support 18 may be positioned between support member 12' and membrane 16'.

The materials, shapes, attributes and other selection criteria used for support 18' may be the same as those used for support 18 as previously disclosed. In one embodiment, 18' will define minimally, a perimeter "band" superposed about and/or underlying a perimeter of membrane 16'.

The "band" may extend laterally to form an attachment flange, and/or radially inwardly from the perimeter of support member 18' to provide any desired additional filter membrane support toward the center of the membrane. The possible configurations for support member 18' are the same as the illustrative embodiments disclosed for support 18. The hydrophilicity or hydrophobicity of support 18' will often match that of membrane 16'. For gases, a hydrophobic membrane is advantageous to permit gas passage and to prohibit hydrophilic liquid passage.

Similar to the embodiments of the rigid supports shown in FIGS. 1-22, support 18' may be structured with a perimeter "band" and one or a plurality of rods or slats extending from one side or end of the support to the other. When a plurality of rods or slats are used, the rods or slats may be oriented to form a grid with each rod or slat arranged in a substantially orthogonal or angular orientation to the other rods or slats intersected. The rods and/or slats may be integral or modular relative to the perimeter "band." Such a configuration enables support 18' to provide structural support to the center portion of membrane 16 without creating any appreciable impediment to gas and/or fluid flow into the bio-reactive container.

Figure 7:
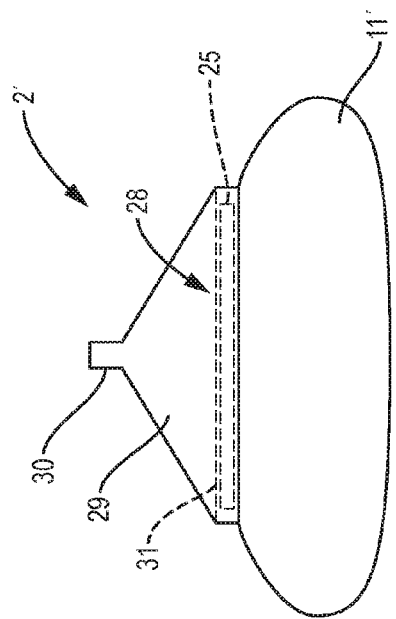
FIG. 7 is a side elevational view in partial phantom of a bio-reactive container with an outlet filer member according to a further embodiment of the disclosure.
Figure 15:
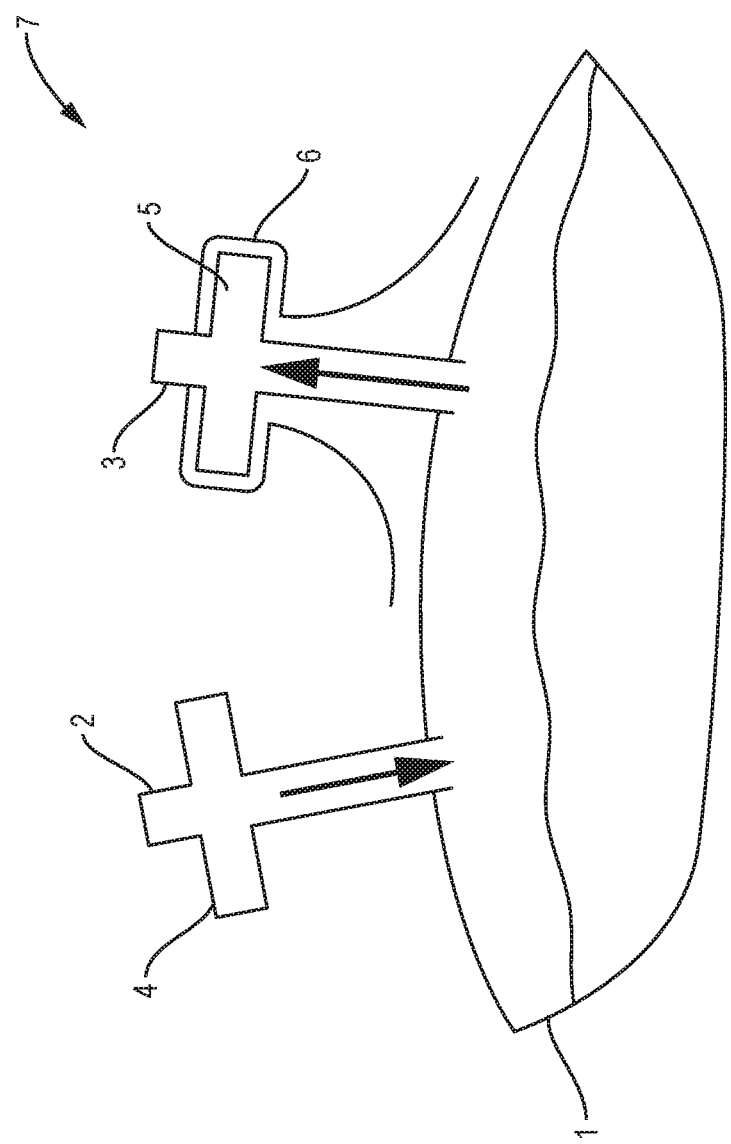
FIG. 15 is a side elevational view of a related art bio-reactive container.

In another aspect of the disclosure shown in FIG. 7, a bio-reactive container assembly is shown designated generally as 2'. Container assembly 2' comprises a bio-reactive container 11' with an outlet assembly or element 28 secured to a top end of container 11'. As used herein, a bio-reactive container outlet assembly or element shall mean an assembly or element secured to a bio-reactive container in place of, or as an adjunct to, a bio-reactive container outlet. In the embodiment shown, an outlet 30 extends from outlet member 28 to permit the release of liquids and/or gases from container assembly 2'. Outlet element 28 may be secured to container 11' on the top, bottom, side, or any combination thereof to accommodate any particular application need with respect to outlet orientation.

Outlet member 28 is structured as a rigid filter support/outlet funnel structure that provides the main support structure for an outlet filter membrane 25 (shown in phantom). Outlet member 28 has portions that define an outlet 30 that may be cylindrical in cross-section, or may be structured with different cross-sectional shapes and include features such as illustratively, barbs, threading, locking features, quick connects (not shown), tri-clamps (not shown) or like connection devices to secure outlet 30 to collection vessels to receive and secure liquids and/or gases exiting container assembly 2'.

A frustoconical section 29 of outlet member 28 extends from a relatively broad end structured to accommodate and support outlet filter membrane 25 proximate to, and in fluid communication with, container 11' to a relatively narrow distal end connected to, and in fluid communication with, outlet 30. The proximal end of outlet member 28 may form a filter membrane support surface or filter seat 31. It should be understood that the frustoconical section may be structured to conform to different geometric shapes or have portions conform to different geometric shapes, e.g., have a rectangular cross-section at the juncture with container 11', and remain within the scope and spirit of the disclosure.

Seat 31 may be formed integrally with outlet member 28, or may be modular in construction and secured to element 28 via thermal bonding, adhesive bonding, mechanical fasteners and like bonding methods. Seat 31 may be formed with a container receiving surface being substantially planar to permit a substantially flat filter membrane to be seated against, and/or secured to, the filter receiving surface. An internally recessed shoulder may also be formed around the perimeter of seat 31 to receive outlet filter membrane 25 and any additional support structures. In this configuration, an outer edge of seat 31 may define a perimeter wall or shoulder that prevents lateral and/or radial displacement of outlet membrane 25 and any additional support structures secured to member 28.

As the total surface area of outlet filter membrane 25 is significantly greater than the relatively small peripheral segment of the membrane that registers against filter seat 31, a substantial portion of membrane 25 is left without structural/mechanical support. Although a rigid filter may not require supplemental support, an optional lower membrane support, such as support 18 for inlet filter membrane 16 may be used to provide additional support and add structural integrity to the membrane peripheral binding region. This is particularly advantageous when relatively high fluid and/or gas pressures are expected to be implemented, or when materials are present in a bio-reactive container, such as liquids including waste liquids having viscosities much higher than the viscosity of a gas. The considerations for a support for outlet membrane 25 are the same as those for inlet filter membrane support 18 with respect to structure and materials. The disclosure regarding support 18 is therefore incorporated here as being equally applicable to the optional support for membrane 25.

Further, the additional supportive structures explained in detail for inlet element 10 may all be applied to outlet element 28. It should be understood that in some instances, the order of the support structures relative to each other or in relation to the membrane may be altered in order to allow greater support of the filter membrane, depending on the direction of force applied to the membrane based on the flow through it. For example, support structures could be incorporated on either side of the filter membrane to provide support with bi-directional flow applications, or could be positioned on only the downstream side of the filter element for single direction flow applications. Any combination of supports and support positions, regardless of flow considerations, is within the contemplation and scope of the disclosure.

Figure 8:
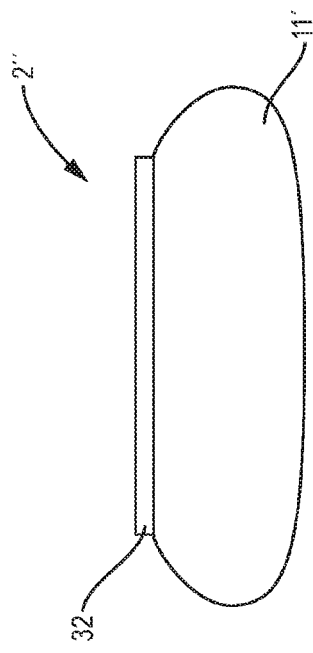
FIG. 8 is a side elevational view of a bio-reactive container with a filter outlet according to a yet further embodiment of the disclosure.

In another aspect of the disclosure, as shown in FIG. 8, a bio-reactive container assembly is shown generally as 2" includes a bio-reactive container 11' combined with an outlet filter element 32. Filter element 32 is secured to container 11' via thermal or sonic bonding, adhesives, mechanical fasteners and the like. Filter element 32 defines from about 10% to about 99% of a top end of a chamber defined collectively by container 11' and filter element 32 and significantly increases the filter surface area available for bulk mass transfer relative to previous bio-reactive container outlet filter systems. In similar fashion to other disclosed inlet and outlet filter embodiments, support structures (similar to supports 18, 20, 22, and the like) may be added to provide structural support for filter element 32.

Referring now to FIG. 9, a bio-reactive container assembly, shown generally as 2'" includes a bio-reactive container 11" with an inlet filter membrane 16" and an outlet filter membrane 32'. Assembly 2'" incorporates the inlet filter membrane of assembly 2 as shown in FIG. 6 with the outlet filter membrane of assembly 2" as shown in FIG. 8. The optional features and optional support structures for filter membrane 16" and outlet membrane 32' are the same as those disclosed for inlet filter membrane 16 and outlet filter membrane 32, respectively, and the disclosure pertaining thereto is incorporated here with respect to membranes 16" and 32'.

Container assembly 2'" includes a filter support member 12" with a laterally extended inlet port 24". Support member 12" is structured to be substantially rigid with a substantially planar surface 13" dimensioned and structured to receive filter member 16". Filter 16" is secured between member 12" and bio-reactive container 11". With this configuration, the combination of support member 12" and filter 16" define a substantial portion of the bottom of container 11" so as to improve and maximize bulk mass transfer into container 11". Like the embodiment shown in FIG. 6, the combination may form and define from about 10% to about 99% of the bottom surface of bio-reactive container assembly 2'".

Support member 12' may further define a perimeter shoulder dimensioned and structured to receive and secure membrane 16". Support member 12" may also have portions defining rods or slats that extend across the perimeter shoulder and the cross-sectional area of member 12" to provide added structural support for membrane 16". The rods or slats may be integral to, or modular relative to, the perimeter shoulder, and may be structured similar to the similar features shown for support 22 in FIGS. 17-22.

If rods or slats are not incorporated into support member 12", or if rods or slats are provided and additional membrane support is required, similar to the embodiments shown in FIGS. 1-5, additional filter membrane support structures may be incorporated into the assembly to provide added structural support to membrane 16". More particularly, a bottom filter support 18" similar in construction to support 18 may be positioned between support member 12" and membrane 16" or a upper filter support 20" similar in construction to support 20 may be positioned between the inner volume of bio-reactive container 11" and membrane 16". The material used for support 18" or 20" may be the same as the materials described as appropriate for use for supports 18 and 20 as disclosed previously herein.

The "band" may extend laterally to form a flange for sealing to other components, and/or radially inwardly from the perimeter of support member 18" or 20" to provide any desired additional filter membrane support toward the center of the membrane. As disclosed for other filter membrane support embodiments, support 18" or 20" must be structured to permit the free passage of liquids and/or gases introduced into the bio-reactive container. In one alternative embodiment, support 18" or 20" may traverse the entire dimensions of membrane 16" to provide maximum support. With this embodiment, support 18" or 20" should be constructed from a porous material having a porosity and pore size great tailored to reduce the resistance to flow while providing the required supportive strength to membrane 16". In one embodiment, the hydrophilicity or hydrophobicity of support 18" or 20" should match that of membrane 16'. As previously disclosed, for gases, a hydrophobic membrane is advantageous to permit gas passage and to substantially prevent aqueous liquid passage.

With respect to an outlet end of container 2''', bio-reactive container assembly 2''' includes bio-reactive container 11" combined with an outlet filter 32". Filter 32" is secured to container 11" via thermal or sonic bonding, adhesives, mechanical fasteners and the like. Filter 32" defines from about 10% to about 99% of a top end of a chamber defined by container 11" and significantly increases the filter surface area available for bulk mass transfer relative to previous bio-reactive container outlet filter systems. In similar fashion to other disclosed embodiments, support structures may be added to provide structural support for filter 32".

Referring now to FIG. 10, a bio-reactive container assembly, shown generally as $2^{iv}$, includes a bio-reactive container 11''' with an inlet filter membrane 16''' and an outlet filter assembly 28'''. Assembly $2^{iv}$ incorporates the inlet filter element of assembly 2 as shown in FIG. 6 with the outlet filter element of assembly 2' as shown in FIG. 7. The materials and optional filter membrane support structures disclosed with respect to the embodiments shown in FIGS. 6 and 7 may be incorporated into this embodiment and the disclosure relative to FIGS. 6 and 7 is incorporated here.

With respect to the outlet end of container assembly $2^{iv}$, outlet assembly or element 28''' is secured to a top end of container 11''' and defines from about 10% to about 99% of a top end of a chamber defined by the combination of the bio-reactive container with the inlet and outlet elements. In the embodiment shown, an outlet 30''' extends from outlet member 28''' to permit the release of liquids and/or gases from container assembly $2^{iv}$.

Outlet member 28''' is structured as a rigid filter support/outlet funnel structure that provides the main support structure for an outlet filter membrane 25''' (shown in phantom). Outlet member 28''' has portions that define an outlet 30''' that may be cylindrical in cross-section, or may be structured with different cross-sectional shapes and features including threading and locking features and the like. Outlet 30''' may also be shaped and structured for adaptation to receive conventional quick connects (not shown), tri-clamps (not shown), barbs (not shown), or like connection devices to secure outlet 30''' to collection vessels to receive and secure liquids and/or gases exiting container assembly $2^{iv}$.

A frustoconical section 29''' of outlet member 28''' extends from a relatively broad end structured to accommodate and support outlet filter membrane 25''' proximate to, and in fluid communication with, container 11''' to a relatively narrow distal end connected to, and in fluid communication with, outlet 30'''. The proximal end of outlet member 28''' may form a filter membrane support surface or filter seat 31''' (shown in phantom). It should be understood that the frustoconical section may be structured to conform to different geometric shapes or have portions conform to different geometric shapes, e.g., have a rectangular cross-section at the juncture with container 11''', and remain within the scope and spirit of the disclosure.

Seat 31''' may be formed integrally with outlet member 28''', or may be modular in construction and secured to element 28''' via thermal bonding, adhesive bonding, mechanical fasteners and like bonding methods. Seat 31''' may be formed with a container receiving surface being substantially planar to permit a substantially flat filter membrane to be seated against, and/or secured to, the filter receiving surface. An internally recessed shoulder may also be formed around the perimeter of seat 31''' to receive outlet filter membrane 25''' and any additional support structures. In this configuration, an outer edge of seat 31''' may define a perimeter wall or shoulder that prevents lateral and/or radial displacement of outlet membrane 25''' and any additional support structures secured to member 28'''.

As the total surface area of outlet filter membrane 25''' is significantly greater than the relatively small peripheral segment of the membrane that registers against filter seat 31''', similar to other embodiments disclosed, a substantial portion of membrane 25''' is left without structural/mechanical support. To the extent structural support is required, supports, both flexible and rigid, upper and/or lower, and similar to those disclosed to support the other disclosed membrane embodiments, may be used with this bio-reactive container assembly embodiment such as support 18 or 20, and rigid support 22 and the various embodiments of those two supports disclosed herein.

Referring now to FIG. 11, a bio-reactive container assembly, shown generally as $2^v$, includes bio-reactive container $11^{iv}$ with an inlet filter assembly $12^{iv}$ and an outlet filter membrane $32^{iv}$. Assembly $2^v$ incorporates the inlet filter assembly shown in FIGS. 1 and 2 and the outlet filter membrane of assembly 2" shown in FIG. 8.

Container assembly $2^v$ includes a rigid filter support/inlet funnel structure shown designated generally as $12^{iv}$ provides the main support structure for the element. Support structure $12^{iv}$ has portions that define an inlet $24^{iv}$ that may be cylindrical in cross-section, or may be structured with different cross-sectional shapes and features including threading, locking features and the like. Inlet $24^{iv}$ may also be shaped and structured for adaptation to receive conventional quick connects (not shown), tri-clamps (not shown), barbs (not shown), or like connection devices to secure inlet $24^{iv}$ to fluid and/or gas supply sources. A frustoconical section of support structure $12^{iv}$ expands from a relatively narrow end proximate, and in fluid communication with, inlet $24^{iv}$ to a relatively broad distal end structured to accommodate and ultimately support a filter membrane $16^{iv}$. The distal end of support structure $12^{iv}$ forms a filter membrane support surface or filter seat $14^{iv}$.

Seat $14^{iv}$ may be formed integrally with support structure $12^{iv}$, or may be modular in construction to be secured to structure $12^{iv}$ via thermal bonding, adhesive bonding, mechanical fasteners and like bonding methods. Seat $14^{iv}$ may be formed to be substantially planar to permit a substantially flat filter membrane to be seated against and/or secured to the filter receiving surface. An internally recessed shoulder may also be formed around the perimeter of seat $14^{iv}$ to receive filter membrane $16^{iv}$ and any additional support structures. In this configuration, an outer edge of seat $14^{iv}$ may define a perimeter wall that prevents lateral or radial displacement of membrane $16^{iv}$ and any additional support structures secured to structure $12^{iv}$.

As the total surface area of filter membrane $16^{iv}$ is significantly greater than the relatively small peripheral segment of the membrane that registers against filter seat $14^{iv}$, a substantial portion of membrane $16^{iv}$ is left without structural/mechanical support. To the extent structural support is required, supports, both flexible and rigid, upper and/or lower, and similar to those disclosed to support the other disclosed membrane embodiments, may be used with this bio-reactive container assembly embodiment such as supports 18 or 20 and rigid support 22 and the various embodiments of those supports disclosed herein.

With respect to the outlet end of container assembly $2^{vi}$, the assembly includes a bio-reactive container $11^v$ combined with an outlet filter $32^v$. Filter $32^v$ is secured to container $11^v$ via thermal or sonic bonding, adhesives, mechanical fasteners and the like. Filter $32^v$ defines a top end of a chamber defined by container $11^v$ and significantly increases the filter surface area available for bulk mass transfer relative to previous bio-reactive container outlet filter systems. In similar fashion to other disclosed embodiments, support structures (membrane, rigid, upper, and lower), may be added to provide structural support for filter $32^v$.

Referring now to FIG. 12, a bio reactive container assembly, shown generally as $2^{vi}$, includes bio-reactive container $11^v$ with an inlet filter assembly $12^v$ and an outlet filter assembly $28^v$. Assembly $2^{vi}$ incorporates the inlet filter assembly shown in FIGS. 1 and 2 and the outlet filter assembly shown in FIG. 7.

Container assembly $2^{vi}$ includes a rigid filter support/inlet funnel structure shown designated generally as $12^v$ provides the main support structure for the element. Support structure $12^v$ has portions that define an inlet $24^v$ that may be cylindrical in cross-section, or may be structured with different cross-sectional shapes and features including threading, locking features and the like. Inlet $24^v$ may also be shaped and structured for adaptation to receive conventional quick connects (not shown), tri-clamps (not shown), barbs (not shown), or like connection devices to secure inlet $24^v$ to fluid and/or gas supply sources. A frustoconical section of support structure $12^v$ expands from a relatively narrow end proximate, and in fluid communication with, inlet $24^v$ to a relatively broad distal end structured to accommodate and ultimately support a filter membrane $16^v$. The distal end of support structure $12^{iv}$ forms a filter membrane support surface or filter seat $14^v$.

Seat 14 may be formed integrally with support structure $12^v$, or may be modular in construction to be secured to structure $12^v$ via thermal bonding, adhesive bonding, mechanical fasteners and like bonding methods. Seat $14^v$ may be formed to be substantially planar to permit a substantially flat filter membrane to be seated against and/or secured to the filter receiving surface. An internally recessed shoulder may also be formed around the perimeter of seat $14^v$ to receive filter membrane $16^v$ and any additional support structures. In this configuration, an outer edge of seat $14^v$ may define a perimeter wall that prevents lateral or radial displacement of membrane $16^v$ and any additional support structures secured to structure $12^v$.

As the total surface area of filter membrane $16^v$ is significantly greater than the relatively small peripheral segment of the membrane that registers against filter seat $14^v$, a substantial portion of membrane $16^v$ is left without structural/mechanical support. To the extent structural support is required, supports, both flexible and rigid, upper and/or lower, and similar to those disclosed to support other membrane embodiments, may be used with this bio-reactive container assembly embodiment such as support 18 or 20 and rigid support 22 and the various embodiments of those two supports disclosed herein.

To ensure a tight seal between a bio-reactive container and inlet member $10^v$, an optional upper rigid support member $22^v$ is secured to a top surface of membrane $16^v$, or to a top surface of an upper membrane support $20^v$, if used. Upper member $22^v$ may be constructed from similar materials used for support structure $12^v$, or may be constructed from different materials that impart the desired rigidity or flexibility to accommodate the rigidity or flexibility of the bio-reactive container material. Suitable materials for upper member $22^v$ include the same materials disclosed for upper member 22 as disclosed herein. The same criteria used to select the materials for upper membrane 22, e.g., compatibility with the liquids and/or gases to be introduced into, or formed in, the bio-reactive container, apply with equal force here with respect to the selection of materials to construct upper membrane $22^v$.

The filter membrane and any optional support structures used (flexible and/or rigid) form a membrane assembly, inlet element $10^v$, and may be secured together via thermal or sonic bonding. Adhesives and the like may also be used. To provide added structural integrity to the layers, a sealing band $26^v$ (not shown, but similar to sealing band 26 shown in FIG. 1, may be superposed about the layers and heat shrunk, thermally or sonically welded and/or adhered to the various layers. Suitable materials for band $26^v$ include the same materials disclosed for sealing band 26.

With respect to the outlet end of container assembly $2^{vi}$, container assembly $2^{vi}$ comprises bio-reactive container $11^v$ with an outlet assembly or element $28^v$ secured to a top end of container $11^v$. As used herein, a bio-reactive container outlet assembly or element shall mean an assembly or element secured to a bio-reactive container in place of, or as an adjunct to, a bio-reactive container outlet. In the embodiment shown, an outlet $30^v$ extends from outlet member $28^v$ to permit the release of liquids and/or gases from container assembly $2^{vi}$.

Outlet member $28^v$ is structured as a rigid filter support/outlet funnel structure that provides the main support structure for an outlet filter membrane $25^v$ (shown in phantom). Outlet member $28^v$ has portions that define an outlet $30^v$ that may be cylindrical in cross-section, or may be structured with different cross-sectional shapes and features including threading, locking features and the like. Outlet $30^v$ may also be shaped and structured for adaptation to receive conventional quick connects (not shown), tri-clamps (not shown), barbs (not shown), or like connection devices to secure outlet $30^v$ to collection vessels to receive and secure liquids and/or gases exiting container assembly $2^{vi}$. A frustoconical section 29 of outlet member $28^v$ extends from a relatively broad end structured to accommodate and support outlet filter membrane $25^v$ proximate to, and in fluid communication with, container $11^v$ to a relatively narrow distal end connected to, and in fluid communication with, outlet $30^v$. The proximal end of outlet member $28^v$ may form a filter membrane support surface or filter seat $31^v$. It should be understood that the frustoconical section may be structured to conform to different geometric shapes or have portions conform to different geometric shapes, e.g., have a rectangular cross-section at the juncture with container $11^v$, and remain within the scope and spirit of the disclosure.

Seat $31^v$ may be formed integrally with outlet member $28^v$, or may be modular in construction and secured to element $28^v$ via thermal bonding, adhesive bonding, mechanical fasteners and like bonding methods. Seat $31^v$ may be formed with a container receiving surface being substantially planar to permit a substantially flat filter membrane to be seated against, and/or secured to, the filter receiving surface. An internally recessed shoulder may also be formed around the perimeter of seat $31^v$ to receive outlet filter membrane $25^v$ and any additional support structures. In this configuration, an outer edge of seat $31^v$ may define a perimeter wall or shoulder that prevents lateral and/or radial displacement of outlet membrane $25^v$ and any additional support structures secured to member $28^v$.

As the total surface area of outlet filter membrane 25 is significantly greater than the relatively small peripheral segment of the membrane that registers against filter seat 31, a substantial portion of membrane 25 is left without structural/mechanical support. To the extent structural support is required, supports, both flexible and rigid, upper and/or lower, and similar to those disclosed to support other membrane embodiments, may be used with this bio-reactive container assembly embodiment such as support 18 or 20 and rigid support 22 and the various embodiments of those supports disclosed herein.

Referring now to FIG. 13, a bio-reactive container assembly is shown designated generally as $2^{vii}$ comprises a bio-reactive container $11^{vi}$ and a hybrid inlet/outlet element $12^{vi}$ structured to deliver and to receive liquids and/or gases to and from the bio-reactive container. Each inlet or outlet element designated generally as 12 or 28 and disclosed herein could be structured with one or multiple ports to allow one or more connections to external elements including, but not limited to pumps, air sources, or even simply open to atmosphere. A single layer or dual layer membrane $16^{vi}$ is secured in inlet/outlet element $12^{vi}$ or between element $12^{vi}$ and bio-reactive container $11^{vi}$.

An inlet $24^{vi}$ is formed on a first end of element $12^{vi}$ to receive liquids and/or gases introduced into the bio-reactive container assembly. Inlet $24^{vi}$ may be formed with, or have attached thereto, a check valve, quick-connect, or other attachment feature to permit attachment to fluid and/or gas sources.

An outlet port $30^{vi}$ is formed on a second end of element $12^{vi}$ to permit the egress of liquids and/or gases from the bio-reactive container assembly. Outlet $30^{vi}$ may be formed with, or have attached thereto, a check valve, quick-connect, or other attachment feature to permit attachment to tubes or other features to receive fluid and/or gas from assembly $2^{vii}$.

If the primary purpose of element $12^{vi}$ is to permit the passage of liquids into the bio-reactive container, a single hydrophilic membrane may be used for this purpose. The membrane may be formed or constructed from hydrophilized polyethersulfone, hydrophilized PVDF, nylon, hydrophilized polyethylene as well as other materials used to construct hydrophilic membranes, as is well known in the art. The membrane may also have pore sizes from about 0.2 nanometers to about 0.5 micrometers. A pore size range from about 0.2 micrometers to about 0.5 micrometers is expected to provide superior results for many bio-bag applications where liquid is drawn off or added to the bio-reactive container.

The membrane is secured to element $12^{vi}$ and/or bio-bag container $11^{vi}$ by thermal bonding, sonic bonding, adhesive, mechanical fasteners and the like. With this configuration, the internal volume of element $12^{vi}$ can be pressurized (with respect to the internal pressure of the bio-reactive container) with liquid (by way of a pump or other means) to preferentially allow the flow of liquid into the bio-reactive container. Alternatively, internal volume of element $12^{vi}$ can be maintained at a negative pressure (relative to the pressure within the bio-reactive container) (by way of a pump or other means) to preferentially allow the flow of liquid out of the bio-reactive container. By adjusting between positive and negative pressure within element $12^{vi}$, the flow into and out of the bio-reactive container can be controlled. Alternatively, the pressure within element $12^{vi}$ can be maintained at or about the pressure within the bio-reactive container to allow for the diffusion-based passage of liquid across the membrane, while restricting the passage of material too large to flow through the pores of the membrane. Liquid can be brought in through inlet $24^{vi}$ and through outlet $30^{vi}$ to maintain or control the nature and concentration of fluid within element $12^{vi}$ which can, in turn, be used to control the diffusional flux across the membrane based on concentration gradient.

With this configuration, the internal volume of element $12^{vi}$ can alternatively be maintained at a positive gas pressure (relative to the pressure within the bio-reactive container) (by way of a pressurized source, pump, or other means) to promote the transfer of gas into the bio-reactive container. Though the bulk flow of gas will be restricted at pressures below the hydrophilic membrane's bubble point, as is well known in the art, diffusional gas flow across the membrane will exist (so long as the pressure is enough to overcome the head pressure of the liquid within the bio-reactive container) at a rate proportional to pressure of the gas, as is also well known in the art. With the liquid within the bio-reactive container in contact with the membrane and with an increased pressure within the internal volume of element $12^{vi}$ relative to that within the bio-reactive container, a concentration driving force may exist capable of promoting the flow of gas into the liquid within the bio-reactive container. However, if the pressure does not overcome the head pressure, bulk liquid may flow into the internal volume of element $12^{vi}$, which may be unwanted.

If gasification is the primary purpose of element $12^{vi}$, a single hydrophobic membrane may be used to prevent the introduction or removal of liquids from container $2^{vii}$. The membrane may be formed or constructed from polytetrafluoroethylene, polyethylene, polyvinylidene, polypropylene, as well as other materials used to construct hydrophobic membranes, as is well known in the art. The membrane may also have pore sizes from about 0.2 nanometers to about 0.5 micrometers. A pore size range from about 0.2 micrometers to about 0.5 micrometers is expected to provide superior results for most conventional bio-bag applications.

The membrane is secured to element $12^{vi}$ and/or bio-bag container $11^{vi}$ by thermal bonding, sonic bonding, adhesive, mechanical fasteners and the like. With this configuration, the internal volume of element $12^{vi}$ can be pressurized (with respect to the internal pressure of the bio-reactive container) with gas (by way of a pressurized source, pump, or other means) to preferentially allow the flow of gas into the bio-reactive container. If this were to be done continuously, the use of an outlet assembly, similar to 28 or 32 may be used to allow the gas to escape from the system. Alternatively, the pressure within element $12^{vi}$ can be maintained at or about the pressure within the bio-reactive container to allow for the diffusion-based passage of gas across the membrane, while restricting the passage of material too large (or with too high a surface tension, in the case of liquids within the container) to flow through the pores of the membrane.

With this configuration, internal volume of element $12^{vi}$ can alternatively be maintained at a negative gas pressure (relative to the pressure within the bio-reactive container) (by way of a pump or other means) to promote the transfer of dissolved gas out of the bio-reactive container. With the liquid within the bio-reactive container in contact with the membrane and with a reduced pressure within the internal volume of element $12^{vi}$ relative to that within the bio-reactive container, a concentration driving force may exist capable of degasifying the liquid within the bio-reactive container. However, if the pressure within the internal volume of element $12^{vi}$ becomes higher than that within the bio-reactive container, bulk gas flow may occur into the bio-reactive container, which may be unwanted.

In a further embodiment, a dual layer hydrophilic/hydrophobic membrane $16^{vi}$ can be used to prevent the bulk flow of liquid and gas across the membrane barrier and permit the diffusive transfer of gas into, or out of, a liquid phase inside the bio-reactive container assembly. The combination membrane permits the use of a single interface to control gasification and degasification by way of diffusional-based mass transfer while preventing the bulk flow of gas to or from the liquid phase under variable processing conditions well known in the art.

For dual layer embodiments used for diffusional-based gas transfer, the hydrophilic layer should be positioned to face the bio-reactive container assembly chamber so as to interface directly with any liquid in the chamber. The exposure to the liquid will result in the wetting of the pores of the hydrophilic layer that acts as a barrier to bulk gas flow between the liquid within the container $11^{vi}$ and the gas within element $12^{vi}$. Flow of the liquid within container $11^{vi}$ through the hydrophobic layer will be restricted or impeded due to the non-wetting properties of hydrophobic filter membranes as is well known in the art. The hydrophobic layer, situated facing away from the bio-reactive chamber, will be in integral contact with any gas introduced into the assembly as well with any vacuum source applied to the assembly.

For gasification, atmospheric pressure or a positive pressure gas source is used to drive the transfer of gases to a liquid phase. The concentration of gases on the gas side of the membrane (determined by mixture ratio and pressure) provides the concentration gradient driving force into or even out of the bio-reactive container and therefore can be controlled through control of these parameters. Depending upon the resident conditions (gases used, pressure, membrane types, membrane pore sizes, porosities, etc.), combined with the concentrations of the gas(es) on the gas side and in the liquid phase on the opposite side, there may be some natural transfer of waste gas from the liquid phase into the gas phase. Any waste gas that collects in the head space of the container can be bled off through a conventional vent filter positioned at the top of the container, or directly from the liquid phase via a degasification device of similar construction to the gasification device.

The use of a degasification device in addition to a gasification device may allow for greater control and efficiency when targeting specific dissolved gas concentrations by allowing the user to control the driving force (concentration gradient) for diffusional-based gas transfer out of the bio-reactive container as well as the driving force for diffusional-based gas transfer into the bio-reactive container. A bio-reactive container with a gasification device as well as a degasification device is shown in FIG. 14 and disclosed in further detail below.

For degasification, a vacuum source is used to drive the transfer of gases dissolved in the liquid to the gas phase. An alternative approach is to use gas at ambient pressure and at a mixture/concentration selected to promote transfer of dissolved waste gases from the liquid phase to the gas phase. By adjusting the conditions of gasification and degasification, (and perhaps the head space conditions as well), a significantly higher degree of control can be achieved with respect to the gas concentrations within the liquid phase of a bio-reactive container. To this end, the positive pressure gas source and/or the vacuum source can be swept periodically, or continually, to maintain desired concentrations at the gas-liquid interface. An added advantage is the controlled and efficient transfer of gas without the bubbling of bulk-gas through the liquid phase. As is well known in the art, bubbling can disrupt cell culture growth within a bio-reactive container and can be particularly problematic with respect to "fragile" cell cultures such as stem cells.

In another aspect of the disclosure as shown in FIG. 14, a bio-reactive container assembly designated generally as $2^{viii}$ includes a bio-reactive container 11 and a hybrid segmented inlet/outlet element $12^{vii}$ structured to deliver and to receive liquids and/or gases to and from the bio-reactive container. Element $12^{vii}$ includes a separator wall 29 secured, or formed in the element to partition the element into an inlet chamber 31 and an outlet chamber 33. A single layer or dual layer membrane $16^{vii}$ is secured in inlet/outlet element $12^{vii}$ or between element $12^{vii}$ and bio-reactive container $11^{vii}$.

An inlet $24^{vii}$ is formed on a first end of element $12^{vii}$ to receive liquids and/or gases introduced into the bio-reactive container assembly. Inlet $24^{vii}$ may be formed with, or have attached thereto, one or multiple check valve, quick-connect, or other attachment features to permit attachment to fluid and/or gas sources.

An outlet port $30^{vii}$ is formed on a second end of element $12^{vii}$ to permit the egress of liquids and/or gases from the bio-reactive container assembly. Outlet $30^{vii}$ may be formed with, or have attached thereto, one or multiple check valve, quick-connect, or other attachment features to permit attachment to tubes or other features to receive fluid and/or gas from assembly $2^{viii}$.

Elements $12^{vii}$ and $28^{vii}$ can be structured with the same considerations as other elements denoted generally and respectively as 12 and 28 using single or multiple layers of hydrophilic and/or hydrophobic membranes to promote either bulk flow or diffusional-based transport between the elements $12^{vii}$ and $28^{vii}$ and bio-reactive container $11^{vii}$. Any combination of layers or noted characteristics are within the contemplation and scope of the disclosure.

In another aspect of the disclosure, a single hydrophobic membrane can be used on the outlet side separating outlet chamber 33 from the interior of the bio-reactive container. Use of a hydrophilic membrane in conjunction with a hydrophobic membrane on the outlet side creates a greater boundary layer that reduces efficiency with which liquid with dissolved gases can flow through the liquid/gas interface defined by the hydrophobic membrane. Use of a vacuum on the outlet side promotes the transfer of gas out of the liquid dissolved phase as disclosed previously. The presence of a hydrophilic membrane on the container side would impede or stop gas flow and function as an unnecessarily restrictive boundary layer due to normal fluid dynamics. The hydrophilic membrane combined with the hydrophilic membrane on the outlet side functions as a magnified boundary layer in which bulk transfer of liquid is restricted.

The removal or absence of a hydrophilic layer permits the gas in the liquid dissolved phase to move freely to the hydrophobic boundary layer interface. This can substantially improve the transfer of gas out of the liquid dissolved phase. The benefit of a hydrophilic hydrophobic layer as explained previously, is the prevention of bulk flow between phases under variable process conditions. As example, if the pressure within the internal volume of element $28^{vii}$ becomes higher than that within the bio-reactive container, bulk gas flow may occur into the bio-reactive container, which may be unwanted.

It should be understood that multiple different combinations are possible with respect to the filter membrane configurations used with container assembly $2^{viii}$. The membrane across inlet chamber 31 and outlet chamber 33 can be a single layer of a hydrophobic, hydrophilic, hydrophobic with portions modified to be hydrophilic, or hydrophilic with portions modified to be hydrophobic. The membrane can be a dual layer with one layer hydrophobic and the other hydrophilic with either layer facing the internal container chamber. Alternatively, the membrane over inlet 31 can be a dual layer with a hydrophilic layer and a hydrophobic layer while the membrane over outlet 33 may be a single layer hydrophobic, or hydrophilic. A further alternative is to have a single layer membrane over inlet 31, hydrophobic or hydrophilic, and a dual layer over outlet 33 with a hydrophilic layer and a hydrophobic layer. The configurations each will have advantages and disadvantages depending upon whether the focus of the container configuration is to promote perfusion, or to promote gasification/degasification. Any combination of any set of filter membrane layers, membrane types, pore sizes, etc. are within the contemplation, scope and spirit of this disclosure.

While the present disclosure has been described in connection with several embodiments thereof, it will be apparent to those skilled in the art that many changes and modifications may be made without departing from the true spirit and scope of the present disclosure. Accordingly, it is intended by the appended claims to cover all such changes and modifications as come within the true spirit and scope of the disclosure.

What I claim as new and desire to secure by United States Letters Patent is:

1. A container assembly for performing biological and pharmaceutical processes and reactions comprising:
   an enclosed container having a pliable impermeable container sidewall defining a sidewall bottom end and a pliable impermeable container top wall integral with the side wall;
   a selectively-permeable container bottom wall consisting of a filter membrane filtration barrier secured to the container sidewall bottom end wherein the membrane functions as a bottom end of the container, wherein the combination of the container and the filter membrane define an enclosed chamber, and wherein the filter membrane also functions as an inlet; and,
   an outlet extending from the container, wherein the outlet is in fluid communication with the chamber.

2. The container assembly of claim 1 wherein the assembly further comprises a filter support secured to the assembly wherein the support provides structural reinforcement to the membrane.

3. The container assembly of claim 2 wherein the filter support defines a perimeter shoulder, wherein the filter membrane is dimensioned and structured to fit within the perimeter shoulder.

4. The container assembly of claim 3 further comprising a lower support membrane positioned adjacent a lower side of the filter membrane.

5. The container assembly of claim 4 further comprising an upper support membrane positioned adjacent to an upper side of the filter membrane.

6. The container assembly of claim 5 further comprising a rigid support secured to the upper support membrane.

7. The container assembly of claim 6 further comprising a sealing band superposed about the filter membrane, lower support, upper support and rigid support.

8. The container assembly of claim 1 further comprising a rigid support secured to the filter membrane.

9. The container assembly of claim 1 further comprising an outlet filter membrane secured to the container sidewall.

10. The container assembly of claim 9 wherein the assembly further comprises an outlet filter support secured to the assembly wherein the support provides structural reinforcement to the membrane.

11. The container assembly of claim 10 wherein the filter support defines a perimeter shoulder, wherein the filter membrane is dimensioned and structured to fit within the perimeter shoulder.

12. The container assembly of claim 11 further comprising an outlet membrane lower support membrane positioned adjacent a lower side of the outlet filter membrane.

13. The container assembly of claim 12 further comprising an outlet membrane upper support membrane positioned adjacent to an upper side of the outlet filter membrane.

14. The container assembly of claim 13 further comprising a rigid support secured to the outlet membrane upper support membrane.

15. The container assembly of claim 14 further comprising a sealing band superposed about the outlet filter membrane, outlet membrane lower support, outlet membrane upper support and outlet membrane rigid support.

16. The container assembly of claim 9 further comprising a rigid support secured to the outlet filter membrane.

17. A container assembly for performing biological and pharmaceutical processes and reactions comprising:
   an enclosed container having a pliable impermeable sidewall defining a sidewall top end and a pliable impermeable bottom wall integral with the sidewall;
   a selectively-permeable container top wall consisting of a filter membrane filtration barrier secured to the container sidewall top end wherein the membrane functions as a top end of the container, wherein the combination of the container and the filter membrane define an enclosed chamber, and wherein the filter membrane also functions as an outlet; and,
   an inlet extending from the container in fluid communication with the chamber.

18. The container assembly of claim 17 wherein the assembly further comprises a filter support secured to the assembly adjacent the filter membrane wherein the support provides structural reinforcement to the membrane.

19. The container assembly of claim 18 wherein the filter support defines a perimeter shoulder, wherein the filter membrane is dimensioned to fit within the perimeter shoulder.

20. The container assembly of claim 19 further comprising a lower support membrane positioned adjacent a lower side of the outlet filter membrane and a sealing band superposed about the outlet filter membrane and lower support.

* * * * *